(12) United States Patent
Salamone et al.

(10) Patent No.: US 7,727,545 B2
(45) Date of Patent: Jun. 1, 2010

(54) POLYMERIC FLUORINATED DIOXOLE AND MEDICAL DEVICES COMPRISING SAME

(75) Inventors: Joseph C. Salamone, Boca Raton, FL (US); Derek A. Schorzman, Pittsford, NY (US)

(73) Assignee: Bausch & Lomb Incorporated, Rochester, NY (US)

(*) Notice: Subject to any disclaimer, the term of this patent is extended or adjusted under 35 U.S.C. 154(b) by 1057 days.

(21) Appl. No.: 11/359,665

(22) Filed: Feb. 22, 2006

(65) Prior Publication Data
US 2007/0196431 A1   Aug. 23, 2007

(51) Int. Cl.
C08F 224/00   (2006.01)

(52) U.S. Cl. .................. 424/428; 526/247; 526/252; 526/266; 526/279; 549/279

(58) Field of Classification Search .................. 424/428; 526/266, 279, 252, 247; 549/455
See application file for complete search history.

(56) References Cited

U.S. PATENT DOCUMENTS

| | | | |
|---|---|---|---|
| 3,228,741 A | 1/1966 | Becker | |
| 3,341,490 A | 9/1967 | Burdick et al. | |
| 3,996,187 A | 12/1976 | Travnicek | |
| 3,996,189 A | 12/1976 | Travnicek | |
| 4,136,250 A | 1/1979 | Mueller et al. | |
| 4,153,641 A | 5/1979 | Deichert et al. | |
| 4,486,577 A | 12/1984 | Mueller et al. | |
| 4,540,761 A | 9/1985 | Kawamura et al. | |
| 4,740,533 A | 4/1988 | Su et al. | |
| 4,910,277 A | 3/1990 | Bambury et al. | |
| 4,954,587 A | 9/1990 | Mueller | |
| 5,010,141 A | 4/1991 | Mueller | |
| 5,023,305 A | 6/1991 | Onozuka et al. | |
| 5,034,461 A | 7/1991 | Lai et al. | |
| 5,070,215 A | 12/1991 | Bambury et al. | |
| 5,079,319 A | 1/1992 | Mueller | |
| 5,260,000 A | 11/1993 | Nandu et al. | |
| 5,310,779 A | 5/1994 | Lai | |
| 5,321,108 A | 6/1994 | Kunzler et al. | |
| 5,358,995 A | 10/1994 | Lai et al. | |
| 5,387,662 A | 2/1995 | Kunzler et al. | |
| 5,449,729 A | 9/1995 | Lai | |
| 5,512,205 A | 4/1996 | Lai | |
| 5,674,957 A | 10/1997 | DeSimone et al. | |
| 6,700,023 B1 | 3/2004 | Wheland et al. | |
| 6,870,020 B2 | 3/2005 | Aten et al. | |
| 6,911,509 B1 | 6/2005 | Chung et al. | |
| 6,911,513 B2 | 6/2005 | Kashiwagi et al. | |

FOREIGN PATENT DOCUMENTS

| | | |
|---|---|---|
| EP | 0683181 A1 | 11/1995 |
| EP | 683181 A1 * | 11/1995 |
| WO | WO 96/31792 A1 | 10/1996 |

OTHER PUBLICATIONS

Al-Doaiss et al., "Synthesis and Photoinitiated Cationic Polymerization of Substituted 2-Cyclopropyl-4-methylene-1,3-dioxolanes," Macromol. Chem. Phys., 2001, vol. 202 ( No. 2), p. 270-275.*
Y. Yang et al., "Partially Fluroinated Amorphous Ring Containing Polymers," Polymer Preprints (2004), vol. 45 ( No. 2), p. 730-731.*
Yang et al., "Polymer Preprints, vol. 44, No. 2, p. 862 (2003)."*
Smith et al., "Perfluorocyclobutane Aromatic Polyethers. Synthesis and Characterization of New Siloxane-Containing Fluoropolymers", Macromolecules, vol. 29, pp. 852-860, (1996).*
Yang et al., "J. Org. Chem., vol. 60, pp. 5696-5698 (1995)."
Hung et al., "Thermal Rearrangement of Fluorinated Dioxoles," J. Am. Chem. Soc. (1990), p. 9671-9672.
Lai, "The Role of Bulky Polysiloxanylalkyl Methacrylates in Polyurethane-Polysiloxane Hydrogels," J. of App. Poly. Sci., 1996, p. 1193-1199.
Y. Yang et al., "Synthesis and Properites of Particulaly Flurinated Amorphous Ring Containing Polymers," Macromonomers (2004), p. 7918-7923.
Hung et al., "Fluorinated Dioxolane Olefins and Epoxides," J. Org. Chem., 1993, p. 972-973.
Simmons et al., "Fluoroketones," J. of Amer. Chem. Soc., 1959, p. 2288-2296.
Yang et al., "Synthesis and Properties of Partially Fluorinated Amorphous Ring Containing Polymers: Poly[bis(2,2-difluorovinyl)formal], Poly[bis(2,2-difluorovinyl)difluoroformal], and Poly[bis(1-deuterio-2,2-difluorovinyl)difluoroformal]," Macromol, 2004, p. 7918-7923.

* cited by examiner

*Primary Examiner*—Peter D. Mulcahy
*Assistant Examiner*—Henry Hu
(74) *Attorney, Agent, or Firm*—Joseph Barrera

(57) ABSTRACT

A polymeric material having improved gas permeability comprises units of fluorinated dioxole. The polymeric material may further comprise units of a hydrophobic monomer, a hydrophilic monomer, or combinations thereof. Such a polymeric material is desirably used to produce medical devices, such as ophthalmic devices that provide increased comfort to a user.

9 Claims, No Drawings

POLYMERIC FLUORINATED DIOXOLE AND MEDICAL DEVICES COMPRISING SAME

BACKGROUND OF THE INVENTION

The present invention relates to polymeric fluorinated dioxole and medical devices comprising the same. In particular, the present invention relates to ophthalmic devices comprising polymeric fluorinated dioxole.

Advances in chemistry of materials for medical devices, such as ophthalmic lenses, have increased their compatibility with a body environment and the comfort for their extended use therein. The extended use of contact lenses requires that materials for these lenses allow sufficient rates of transport of oxygen to the cornea to preserve its health because the cornea does not have blood vessels for the supply of oxygen and must receive this gas by its diffusion through the epithelial layer on the outer surface of the cornea.

While there exist rigid gas permeable ("RGP") contact lenses, which have high oxygen permeability and which move on the eye, RGP lenses are typically quite uncomfortable for the wearer. Thus, soft contact lenses are preferred by many wearers because of comfort. (Soft materials are those exhibiting low modulus of elasticity, such as less than about 150 g/mm$^2$.) Moreover, a contact lens which may be continuously worn for a period of a day or more (including wear during periods of sleeping) requires comfort levels that exclude RGP lenses as popular extended-wear candidates. Among the soft contact lens materials having high oxygen permeability have been polymers containing siloxane groups. For example, see U.S. Pat. Nos. 3,228,741; 3,341,490; 3,996,187; and 3,996,189.

Contact lens materials having oxygen permeability up to 60 barrers have been made with combinations of fluorinated alkyl methacrylates and polysiloxane macromers. For example, U.S. Pat. No. 4,486,577 discloses an RGP lens formulation comprising hexafluoroisopropyl methacrylate and poly(dimethylsiloxane) macromer. Another combination is taught in U.S. Pat. Nos. 4,540,761 and 5,023,305, which disclose the addition of trifluoroethyl methacrylate to an RGP-type formulation containing oligosiloxanylalkyl methacrylate.

However, attempts to increase the oxygen permeability by increasing the proportions of siloxane-containing polymers and fluorinated monomers conflict with the need to keep other physical properties, such as hardness and dimensional stability and toughness, at a useful level.

Therefore, there is a continued need to provide materials having improved oxygen permeability but avoiding the limitations of the prior-art materials. In particular, it is very desirable to provide materials for ophthalmic devices, which materials have improved oxygen permeability and physical strength, and at the same time provide comfort to the users.

SUMMARY OF THE INVENTION

In general, the present invention provides fluorinated dioxole, polymeric materials comprising fluorinated dioxole, and medical devices comprising such polymeric materials.

In one aspect, the medical devices of the present invention provides improved gas (such as oxygen) permeability.

In another aspect, the medical devices of the present invention provide a higher level of comfort to the users.

In still another aspect, the medical devices are ophthalmic devices.

In yet another aspect, the medical devices are contact lenses.

In a further aspect, the present invention provides a polymeric material for making ophthalmic devices having improved gas permeability. The polymeric material comprises units of a fluorinated dioxole, wherein the fluorinated dioxole units have formulas of

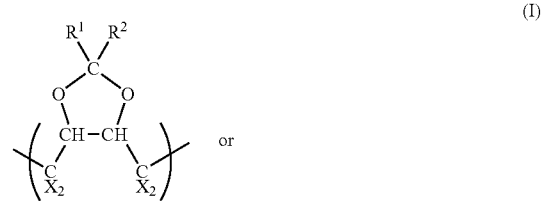

(I)

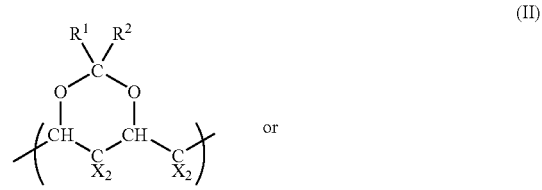

(II)

(III)

or combinations thereof, wherein X is independently selected from the group consisting of hydrogen, fluorine, and $R^3$; $R^1$, $R^2$, and $R^3$ are independently selected from the group consisting of substituted and unsubstituted lower alkyl groups (defined below), substituted and unsubstituted alkyloxy groups, substituted and unsubstituted aromatic and heteroaromatic groups having 6-36 carbon atoms in the ring system, substituted and unsubstituted cyclic and heterocyclic groups having 6-36 carbon atoms in the ring system, and combinations thereof; and at least one of the groups $R^1$, $R^2$, and X comprises a fluorinated group.

In still a further aspect, the polymeric material further comprises siloxane units.

In yet another aspect, the present invention provides a method of making a medical device that has improved oxygen permeability. The method comprises: (a) providing a polymeric material that comprises units of a fluorinated dioxole; and (b) forming the medical device from the polymeric material having improved oxygen permeability.

Other features and advantages of the present invention will become apparent from the following detailed description and claims.

DETAILED DESCRIPTION OF THE INVENTION

The term "lower alkyl" means an alkyl group having any number of carbon atoms from 1 to, and including, 10 (e.g., 1, 2, 3, 4, 5, 6, 7, 8, 9, or 10). A lower alkyl group can be a linear (e.g., having 1-10 carbon atoms), branched (e.g., having 3-10 carbon atoms), or cyclic (e.g., having 3-10 carbon atoms) alkyl. A "substituted" group, as used herein, includes a halogenated group.

The phrase "from i to j" (wherein i and j are exemplary integers in such a phrase) means the range from i to j, including i and j.

The term "(meth)acrylate" includes acrylate and methacrylate. Similar meanings apply to other analogous terms of "(meth)acrylate."

In general, the present invention provides fluorinated dioxole, polymeric materials comprising fluorinated dioxole, medical devices comprising such polymeric materials, and methods of making such devices.

In one aspect, a medical device of the present invention is an ophthalmic device, such as a contact lens, having improved oxygen permeability and comprising a polymeric material that comprises units of a fluorinated dioxole having Formula I, Formula II, Formula II, or combinations thereof.

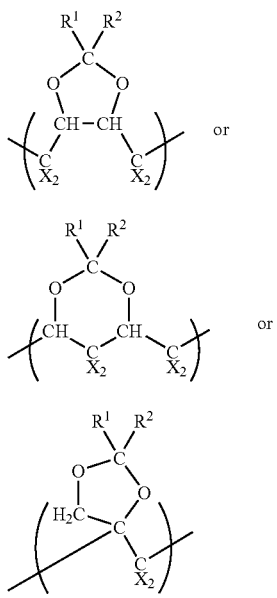

wherein X is independently selected from the group consisting of hydrogen, fluorine, and $R^3$; $R^1$, $R^2$, and $R^3$ are independently selected from the group consisting of substituted and unsubstituted lower alkyl groups, substituted and unsubstituted alkyloxy groups, substituted and unsubstituted aromatic and heteroaromatic groups having 6-36 carbon atoms in the ring system, substituted and unsubstituted cyclic and heterocyclic groups having 6-36 carbon atoms in the ring system, and combinations thereof; and at least one of the groups $R^1$, $R^2$, and X comprises a fluorinated group. In one embodiment, the aromatic groups are selected from the group consisting of phenyl, benzyl, cumenyl, mesityl, tolyl, xylyl, benzhydryl, cinnamyl, phenethyl, styryl, trityl, naphthyl, anthryl, phenanthryl, and combinations thereof. In one embodiment, at least one X is fluorine.

In another embodiment, $R^1$ and $R^2$ are both the trifluoromethyl group, and X is fluorine.

In another embodiment, at least one of $R^1$, $R^2$, and X comprises a substituted or unsubstituted aromatic group having 6-36 carbon atoms in the ring system.

In still another embodiment, at least one of $R^1$, $R^2$, and X comprises a fluorinated aromatic group having 6-36 carbon atoms in the ring system.

In still another embodiment, $R^1$, $R^2$, and X independently comprise fluorinated lower alkyl, such as trifluoromethyl, pentafluoroethyl, heptafluoropropyl, or nonofluorobutyl.

A polymeric material of the present invention that comprises units of fluorinated dioxole is produced by, for example, the polymerization of a fluorinated divinyl ketal monomer, either alone or in combination with another monomer, such as a vinyl monomer.

A fluorinated divinyl ketal monomer (Formula VIII) suitable for the present invention can be prepared according to Scheme 1. The preparation of compound IV is taught in and the first reaction of Scheme 1 may be adapted from Z. Yang, J. Org. Chem., Vol. 60, 5696-98 (1995). The second reaction of Scheme 1 can be adapted from Y. Yang et al., *Polymer Preprints*, Vol. 44, No. 2, 862 (2003).

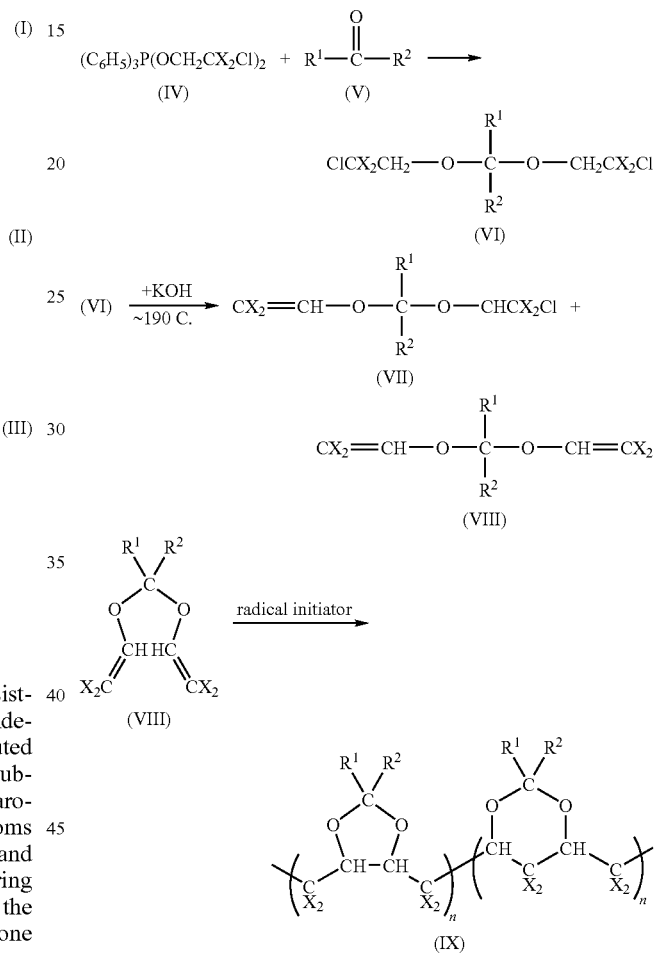

wherein $R^1$, $R^2$, and X are defined above.

The polymerization of the last step of Scheme 1 may be carried out in the presence of a photopolymerization initiator or thermal polymerization initiator selected from those well known in the art.

Thermal polymerization initiators include organic peroxy compounds and azobis(organonitrile) compounds. Non-limiting examples of suitable organic peroxy compounds include peroxymonocarbonate esters, such as tert-butylperoxy isopropyl carbonate; peroxydicarbonate esters, such as di(2-ethylhexyl) peroxydicarbonate, di(sec-butyl)peroxydicarbonate and diisopropyl peroxydicarbonate; diacyl peroxides, such as 2,4-dichlorobenzoyl peroxide, isobutyryl peroxide, decanoyl peroxide, lauroyl peroxide, propionyl peroxide, acetyl peroxide, benzoyl peroxide, p-chlorobenzoyl peroxide; peroxyesters, such as t-butylperoxy pivalate, tert-butylperoxy octylate, and tert-butylperoxy isobutyrate; methylethylketone peroxide; and acetylcyclohexane sulfonyl peroxide. Non-limiting examples of suitable azobis(organonitrile) compounds include azobis(isobutyronitrile); 2,2'-azobis(2,4-dimethylpentanenitrile); 1,1'-azobiscyclohexanecarbonitrile; and azobis(2,4-dimethylvaleronitrile); and mixtures thereof. Preferably, such an initiator is employed in a concentration of approximately 0.01 to 1 percent by weight of the total monomer mixture.

Other suitable thermal polymerization initiators are halogenated initiators including, for example, chlorinated and fluorinated initiators, which are capable of decomposing into free radical species. Initiators which are soluble in the polymerization medium are preferred. For example, non-limiting examples of suitable polymerization initiators include chlorocarbon- or chlorohydrocarbon-based and fluorocarbon- or fluorohydrocarbon-based acyl peroxides such as trichloroacetyl peroxide; bis(perfluoro-2-propoxypropionyl) peroxide $((CF_3CF_2CF_2OCF(CF_3)COO)_2)$; perfluoropropionyl peroxides $((CF_3CF_2CF_2 COO)_2, (CF_3CF_2COO)_2, \{(CF_3CF_2CF_2)CF(CF_3)CF_2O\}_nCF(CF_3)COO\}_2$, $(ClCF_2(CF_2)_nCOO)_2$, where n=0-8); perfluoroalkyl azo compounds such as perfluoroazoisopropane $((CF_3)_2CFN=)_2$; R'''N=NR''', where R''' is a linear or branched perfluorocarbon group having 1-8 carbons; stable or hindered perfluoroalkane radicals such as hexafluoropropylene trimer radical $(((CF_3)_2CF)_2(CF_2CF_2)C$. radical and perfluoroalkanes); perfluorobenzoyl peroxide; 2,3-bis(difluoroamino)perfluoro-2-butene; trifluoromethyl peroxide; $N_2F_2$; $FSO_2NF_2$; $CF_3C(NF_2)=C(NF_2)CF_3$. Preferably, the initiator is a fluorinated initiator, and more preferably the initiator is selected from the group consisting of bis(perfluoro-2-propoxypropionyl) peroxide, perfluoropropionyl peroxide, perfluoroazoisopropane, and hexafluoropropylene trimer radical.

Representative UV photopolymerization initiators include those known in the field, such as the classes of benzophenone and its derivatives, benzoin ethers, and phosphine oxides. Some non-limiting examples of these initiators are benzophenone; 4,4'-bis(dimethylamino)benzophenone; 4,4'-dihydroxybenzophenone; 2,2-diethoxyacetophenone; 2,2-dimethoxy-2-phenylacetophenone; 4-(dimethylamino) benzophenone; 2,5-dimethylbenzophenone; 3,4-dimethybenzophenone; 4'-ethoxyacetophenone; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; 4'-phenoxyacetophenone; 2-methyl-4'-(methylthio)-2-morpholinopropiophenone; benzoin methyl ether; benzoin ethyl ether; diphenyl(2,4,6-trimethylbenzoyl)phosphine oxide. These initiators are commercially available. Other photo polymerization initiators are known under the trade names Darocur™ and Irgacure™, such as Darocur™ 1173 (2-hydroxy-2-methyl-1-phenyl-1-propanone), Irgacure™ 651 (2,2-dimethoxy-2-phenylacetophenone), Irgacure™ 819 (phenyl-bis(2,4,6-trimethyl benzoyl)phosphine oxide), and Irgacure™ 184 (1-hydroxy cyclohexyl phenyl ketone) from Ciba-Geigy, Basel, Switzerland. Other desirable photopolymerization initiators are those activatable by visible light, for example, blue light.

Example 1

Synthesis of $(C_6H_5)_3P(OCH_2CF_2Cl)_2$ (a Species Represented by Formula IV)

This synthesis is adapted from Z. Yang, *J. Org. Chem.*, Vol. 60, 5696-98 (1995). To a stirred solution of 30 g (0.115 mol) of $(C_6H_5)_3P$ in 300 ml of $CH_2Cl_2$ is added a solution of 18.3 g (0.115 mol) of $Br_2$ in 100 ml of $CH_2Cl_2$ at −40° C. over one hour. After the addition is complete, the mixture is stirred while the temperature is brought to room temperature for one hour, and then cooled back to −40° C. A mixture of 25 g (0.21 mol) of $ClCF_2CH_2OH$ and 21.2 g (0.21 mol) of $C_2H_5N$ in 100 ml of ether and 100 ml $CH_2Cl_2$ is added at this temperature over one hour, and then the resulting mixture is warmed to room temperature and stirred for an additional 3.5 hours. After the solids are removed by filtration under nitrogen and the filtrate is evaporated under vacuum at room temperature, a quantity of 50.1 g of $(C_6H_5)_3P(OCH_2CF_2Cl)_2$ is obtained.

Similarly, $(C_6H_5)_3P(OCH_2CX_2Cl)_2$ may be prepared by using $(C_6H_5)_3P$ and $ClCX_2CH_2OH$, wherein X is defined above.

Example 2

Synthesis of $(CF_3)_2C(OCH_2CF_2Cl)_2$ (a Species Represented by Formula VI)

A solution of 450.1 g of $(C_6H_5)_3P(OCH_2CF_2Cl)_2$, which is prepared according to Example 1, in 300 ml $CH_2Cl_2$ is transferred into a 1-liter autoclave under nitrogen and then the autoclave is pressurized with 180 g of hexafluoroacetone. After being heated at 150° C. for 3 hours and at 200° C. for 4 hours, the reaction mixture is poured into a flask and distilled to give the desired product $(CF_3)_2C(OCH_2CF_2Cl)_2$.

Similarly, $(R^1)(R^2)C(OCH_2CX_2Cl)_2$ may be prepared by using $(C_6H_5)_3P(OCH_2CX_2Cl)_2$ instead of $(C_6H_5)_3P(OCH_2CF_2Cl)_2$, and $(R^1)(R^2)C(OCH_2CX_2Cl)_2$ instead of $(CF_3)_2C(OCH_2CF_2Cl)_2$.

Example 3

Synthesis of $CF_2=CH-O-(C)(CF_3)_2-O-CH=CF_2$ (a Species Represented by Formula VIII)

To a molten KOH at 190° C. is slowly added 21.8 g of $(CF_3)_2C(OCH_2CF_2Cl)_2$, which is prepared according to Example 2. The reaction product is condensed in a dry ice trap. The condensed mixture comprises compounds having Formulas X and Xl.

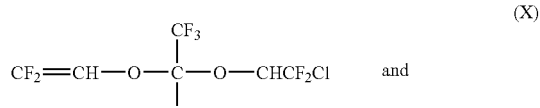

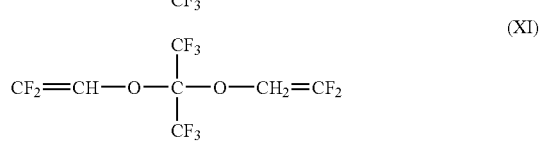

The mixture is distilled to separate compound of Formula X from compound of Formula XI.

Similarly, $CX_2=CH-O-C(R^1)(R^2)-O-CH=CX_2$ may be prepared by using $(R^1)R^2)C(OCH_2CF_2Cl)_2$ instead of $(CF_3)_2C(OCH_2CF_2Cl)_2$.

Example 4

Synthesis of Polymer Comprising Units of Fluorinated Dioxole

Compound XI is polymerized using a photopolymerization initiator such as Darocurm™1173 under UV radiation to obtain a polymer having repeating units represented by Formula XII.

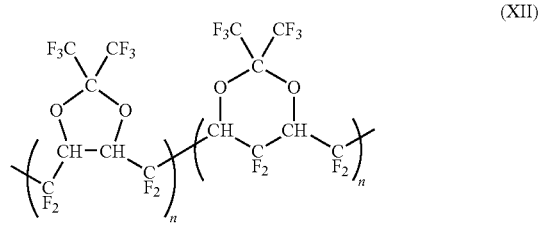
(XII)

Similarly, a polymer having repeating units represented by Formula IX may be prepared by polymerization of monomeric divinyl ketal having Formula VIII in the presence of a thermal polymerization initiator or a photo polymerization initiator.

In another aspect, the present invention provides a polymeric material comprising units represented by Formula III. Such a polymeric material is prepared by a radical polymerization of monomeric units having Formula XIII.

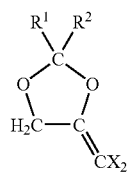
(XIII)

wherein $R^1$, $R^2$, and X are defined above.

A polymerizable dioxole represented by Formula XVII (a species of the dioxole having Formula XIII) can be prepared according to Scheme 2.

Scheme 2

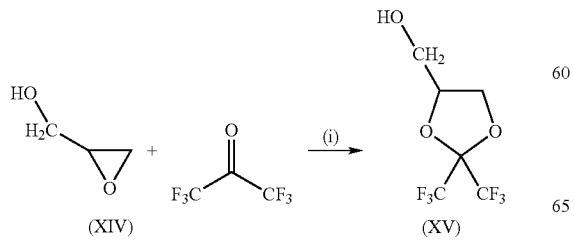

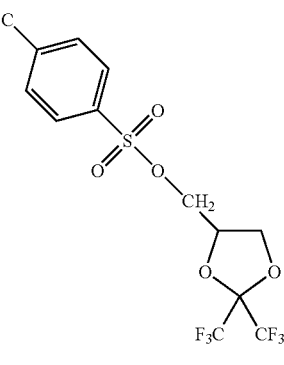
(XV)

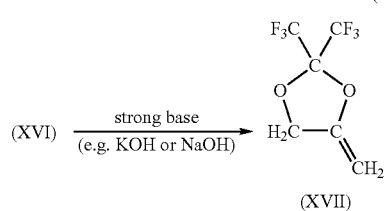
(XVI)

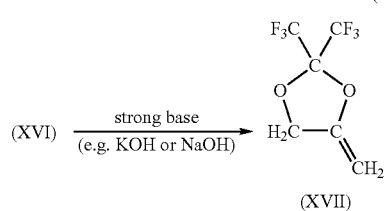
(XVII)

Reaction (i) is carried out in the presence of n-BU$_4$NBr (0.15 weight percent) and water (0.15 weight percent) at about 125° C. for about 5 hours with a yield of about 93 percent. See *J. Am. Chem. Soc.*, Vol. 112, 9672 (1990). Fluorinated dioxole having Formula XVI can be polymerized by radical polymerization to provide a polymer of the present invention.

Similarly, a polymerizable dioxole represented by Formula XIII can be prepared according to Scheme 3.

Scheme 3

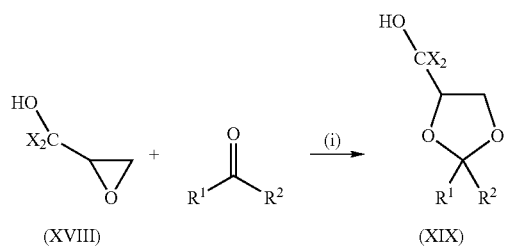
(XVIII) (XIX)

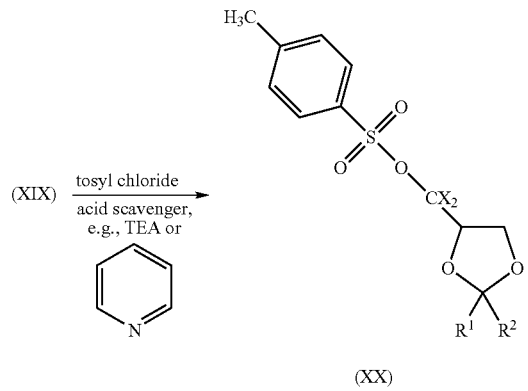
(XX)

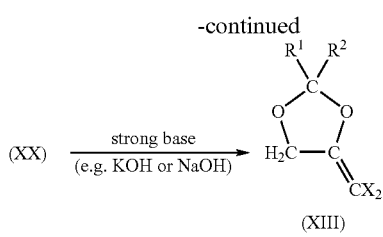

wherein the condition of reaction (i) is disclosed above; and $R^1$, $R^2$, and X are defined above.

Fluorinated dioxole of Formula XIII can be polymerized to provide a polymer of the present invention comprising units having Formula III.

In one aspect, the present invention provides a method for producing a polymerizable fluorinated dioxole. The method comprises: (a) reacting a hydroxy-functionalized epoxide with a ketone that comprises at least a fluorinated group to produce a hydroxy-functionalized fluorinated dioxole; (b) converting the hydroxy-functionalized fluorinated dioxole to a strong-acid fluorinated dioxole ester; and (c) converting the strong-acid fluorinated dioxole ester to the polymerizable fluorinated dioxole in the presence of a strong base. In one embodiment, the step of converting the hydroxy-functionalized fluorinated dioxole to a strong-acid fluorinated dioxole ester comprises reacting the hydroxy-functionalized fluorinated dioxole with a sulfonyl chloride, such as tosyl chloride (p-toluenesulfonyl chloride), mesitylene sulfonyl chloride, combinations thereof, or mixtures thereof. In another embodiment, non-limiting examples of the strong base employed in step (c) are potassium hydroxide, sodium hydroxide, lithium hydroxide, rubidium hydroxide, cesium hydroxide, magnesium hydroxide, strontium hydroxide, barium hydroxide, calcium hydroxide, combinations thereof, and mixtures thereof.

Polymeric materials of the present invention comprising units of fluorinated dioxole are advantageously used to produce ophthalmic lenses having improved gas (such as oxygen) permeability. Although the applicants do not wish to be bound by any particular theory, they believe that such polymeric materials have high rigidity of its main chain due to the ring structure of the monomeric units and the bulky pendant groups (such as the —$CF_3$ group), which are oriented perpendicularly to the dioxole rings and prevent their close approach. As a result, the free volume of a polymeric material of the present invention has a high free volume, leading to high gas permeability.

In another aspect, medical devices are made from a polymer that comprises monomeric units of Formula I, II, III, or combinations thereof and units of at least another type of monomers. Such a polymer can be a hydrogel or non-hydrogel material. In general, non-hydrogel materials are hydrophobic polymeric materials that do not contain water in their equilibrium state. Typical non-hydrogel materials comprise silicone acrylics, such as those formed from bulky silicone monomer (e.g., tris(trimethylsiloxy)silylpropyl methacrylate, commonly known as "TRIS" monomer), methacrylate end-capped poly(dimethylsiloxane) prepolymer, or silicones having fluoroalkyl side groups. On the other hand, hydrogel materials comprise hydrated, crosslinked polymeric systems containing water in an equilibrium state. Hydrogel materials contain about 5 weight percent water or more (up to, for example, about 80 weight percent). Non-limiting examples of materials suitable for the manufacture of medical devices, such as contact lenses, are herein disclosed.

Hydrogel materials for medical devices, such as contact lenses, can comprise a hydrophilic monomer, such as, HEMA, methacrylic acid ("MAA"), acrylic acid ("AA"), methacrylamide, acrylamide, N,N'-dimethylmethacrylamide, or N,N'-dimethylacrylamide; copolymers thereof; hydrophilic prepolymers, such as poly(alkylene oxide) having varying chain length, functionalized with polymerizable groups; and/or silicone hydrogels comprising siloxane-containing monomeric units and at least one of the aforementioned hydrophilic monomers and/or prepolymers. Hydrogel materials also can comprise a cyclic lactam, such as N-vinyl-2-pyrrolidone ("NVP"), or derivatives thereof. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

Silicone hydrogels generally have water content greater than about 5 weight percent and more commonly between about 10 to about 80 weight percent. Such materials are usually prepared by polymerizing a mixture containing at least one siloxane-containing monomer and at least one hydrophilic monomer. Typically, either the siloxane-containing monomer or the hydrophilic monomer functions as a crosslinking agent (a crosslinking agent or crosslinker being defined as a monomer having multiple polymerizable functionalities) or a separate crosslinker may be employed. Applicable siloxane-containing monomeric units for use in the formation of silicone hydrogels are known in the art and numerous examples are provided, for example, in U.S. Pat. Nos. 4,136,250; 4,153,641; 4,740,533; 5,034,461; 5,070,215; 5,260,000; 5,310,779; and 5,358,995.

Examples of applicable siloxane-containing monomeric units include bulky siloxanylalkyl(meth)acrylic monomers. The term "(meth)acrylic" means methacrylic or acrylic, depending on whether the term "meth" is present or absent. An example of bulky siloxanylalkyl(meth)acrylic monomers are represented by the following Formula XXII:

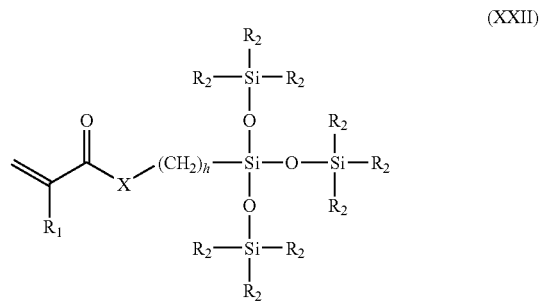

wherein X denotes —O— or —NR—; each $R_1$ independently denotes hydrogen or methyl; each $R_2$ independently denotes a lower alkyl radical, phenyl radical or a group represented by

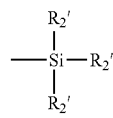

wherein each $R'_2$ independently denotes a lower alkyl, fluoroalkyl, or phenyl radical; and h is 1 to 10. The term "lower alkyl" means an alkyl radical having 1, 2, 3, 4, 5, 6, 7, 8, 9, or 10 carbon atoms, such as methyl, ethyl, propyl, butyl, isobutyl, pentyl, isopentyl, or hexyl radical.

A suitable bulky monomer is 3-methacryloyloxypropyltris(trimethyl-siloxy)silane or tris(trimethylsiloxy)silylpropyl methacrylate ("TRIS").

Another class of representative silicon-containing monomers includes silicone-containing vinyl carbonate or vinyl carbamate monomers such as: 1,3-bis{4-(vinyloxycarbonyloxy)but-1-yl}tetramethyldisiloxane; 3-(trimethylsilyl)propyl vinyl carbonate; 3-(vinyloxycarbonylthio)propyl-{tris(trimethylsiloxy)silane}; 3-{tris(trimethylsiloxy)silyl}propyl vinyl carbamate; 3-{tris(trimethylsiloxy)silyl}propyl allyl carbamate; 3-{tris(trimethylsiloxy)silyl}propyl vinyl carbonate; t-butyldimethylsiloxyethyl vinyl carbonate; trimethylsilylethyl vinyl carbonate; and trimethylsilylmethyl vinyl carbonate.

Another class of representative silicon-containing monomers includes silicone-containing vinyl carbonate or vinyl carbamate monomers such as: 1,3-bis{4-(vinyloxycarbonyloxy)but-1-yl}tetramethyl-disiloxane; 3-(trimethylsilyl)propyl vinyl carbonate; 3-(vinyloxycarbonylthio)propyl-{tris(trimethylsiloxy)silane}; 3-{tris(trimethylsiloxy)silyl}propyl vinyl carbamate; 3-{tris(trimethylsiloxy)silyl}propyl allyl carbamate; t-butyldimethylsiloxyethyl vinyl carbonate; trimethylsilylethyl vinyl carbonate; and trimethylsilylmethyl vinyl carbonate.

An example of silicon-containing vinyl carbonate or vinyl carbamate monomers are represented by Formula XXIII:

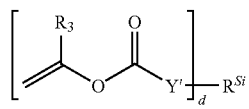

(XXIII)

wherein:

Y' denotes —O—, —S— or —NH—;

$R^{Si}$ denotes a silicon-containing organic radical;

$R_3$ denotes hydrogen or methyl; and d is 1, 2, 3 or 4.

Suitable silicon-containing organic radicals $R^{Si}$ include the following:

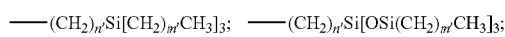

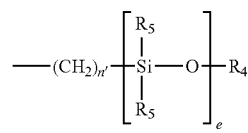

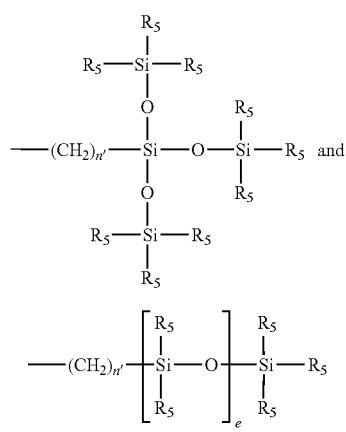

wherein $R_4$ denotes

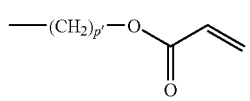

wherein p' is from 1 to and including 6;

$R_5$ denotes an alkyl radical or a fluoroalkyl radical having from 1 to and including 6 carbon atoms;

e is 1 to 200; n' is 1, 2, 3 or 4; and m' is 0, 1, 2, 3, 4 or 5.

An example of a particular species within Formula XXIII is represented by Formula XXIV.

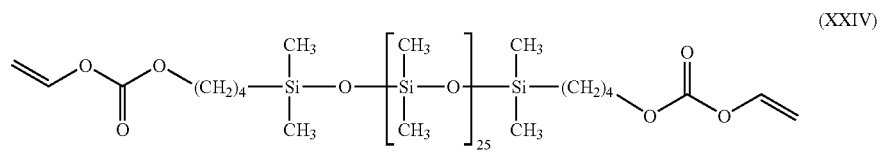

(XXIV)

Another class of silicon-containing monomer includes polyurethane-polysiloxane macromonomers (also sometimes referred to as prepolymers), which may have hard-soft-hard blocks like traditional urethane elastomers. They may be end-capped with a hydrophilic monomer such as HEMA. Examples of such silicone urethanes are disclosed in a variety or publications, including Lai, Yu-Chin, "The Role of Bulky Polysiloxanylalkyl Methacryates in Polyurethane-Polysiloxane Hydrogels," *Journal of Applied Polymer Science*, Vol. 60, 1193-1199 (1996). PCT Published Application No. WO 96/31792 discloses examples of such monomers, which disclosure is hereby incorporated by reference in its entirety. Further examples of silicone urethane monomers are represented by Formulas XXV and XXVI:

(XXV)

or

(XXVI), wherein:

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureylene linkage;

X denotes —CO— or —OCO—;

Z denotes —O— or —NH—;

Ar denotes a substituted or unsubstituted aromatic radical having from 6 to and including 30 carbon atoms;

w is from 0 to and including 6; x is 0 or 1; y is 0 or 1; and z is 0 or 1.

A more specific example of a silicone-containing urethane monomer is represented by Formula XXIX:

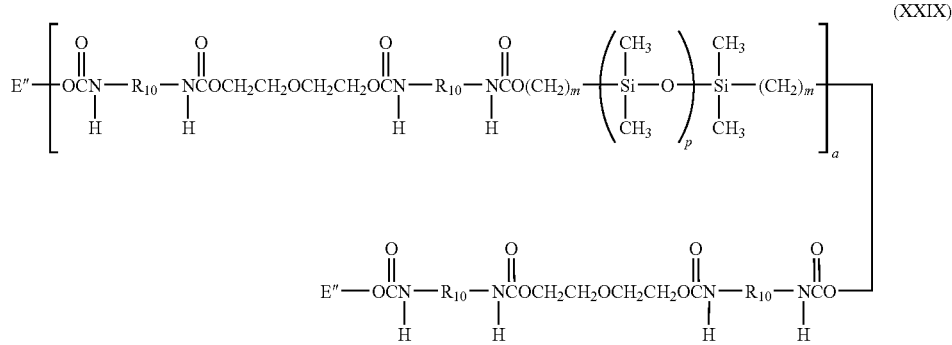

a is at least 1;

A denotes a divalent polymeric radical of Formula XXVII:

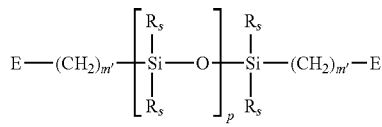

wherein:

each $R_s$ independently denotes an alkyl or fluoro-substituted alkyl group having 1 to 10 carbon atoms which may contain ether linkages between carbon atoms;

m' is at least 1; and p is a number which provides a moiety weight of 400 to 10,000;

each of E and E' independently denotes a polymerizable unsaturated organic radical represented by Formula XXVIII:

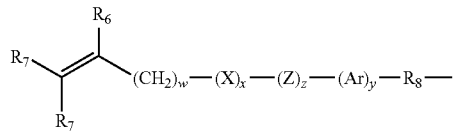

wherein:

$R_6$ is hydrogen or methyl;

$R_7$ is hydrogen, an alkyl radical having from 1 to and including 6 carbon atoms, or a —CO—Y—$R_9$ radical wherein Y is —O—, —S— or —NH—;

$R_8$ is a divalent alkylene radical having from 1 to and including 10 carbon atoms;

$R_9$ is a alkyl radical having from 1 to and including 12 carbon atoms;

wherein m is at least 1 and is preferably 3 or 4, a is at least 1 and preferably is 1, p is a number which provides a moiety weight of 400 to 10,000 and is preferably at least 30, $R_{10}$ is a diradical of a diisocyanate after removal of the isocyanate group, such as the diradical of isophorone diisocyanate, and each E" is a group represented by:

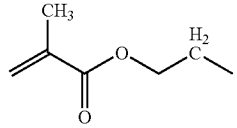

A preferred silicone hydrogel material comprises (in the bulk monomer mixture that is copolymerized) 5 to 50 percent, preferably 10 to 25, by weight of one or more silicone macromonomers, 5 to 75 percent, preferably 30 to 60 percent, by weight of one or more poly(siloxanylalkyl(meth)acrylic) monomers, and 10 to 50 percent, preferably 20 to 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 to Deichert et al. discloses additional unsaturated groups, including acryloxy or methacryloxy. Fumarate-containing materials such as those taught in U.S. Pat. Nos. 5,512,205; 5,449,729; and 5,310,779 to Lai are also useful substrates in accordance with the invention. Preferably, the silane macromonomer is a silicon-containing vinyl carbonate or vinyl carbamate or a polyurethane-polysiloxane having one or more hard-soft-hard blocks and end-capped with a hydrophilic monomer.

In particular regard to contact lenses, the fluorination of certain monomers used in the formation of silicone hydrogels has been indicated to reduce the accumulation of deposits on contact lenses made therefrom, as described in U.S. Pat. Nos. 4,954,587, 5,079,319 and 5,010,141. Moreover, the use of silicone-containing monomers having certain fluorinated side groups (e.g., —(CF₂)—H) have been found to improve compatibility between the hydrophilic and silicone-containing monomeric units, as described in U.S. Pat. Nos. 5,387,662 and 5,321,108.

In another aspect, a polymeric material of the present invention comprises an additional monomer selected from the group consisting of hydrophilic monomers and hydrophobic monomers.

Hydrophilic monomers can be nonionic monomers, such as 2-hydroxyethyl methacrylate ("HEMA"), 2-hydroxyethyl acrylate ("HEA"), 2-(2-ethoxyethoxy)ethyl(meth)acrylate, glyceryl(meth)acrylate, poly(ethylene glycol (meth)acrylate), tetrahydrofurfuryl(meth)acrylate, (meth)acrylamide, N,N'-dimethylmethacrylamide, N,N'-dimethylacrylamide ("DMA"), N-vinyl-2-pyrrolidone (or other N-vinyl lactams), N-vinyl acetamide, and combinations thereof. Other hydrophilic monomers can have more than one polymerizable group, such as tetraethylene glycol (meth)acrylate, triethylene glycol (meth)acrylate, tripropylene glycol (meth)acrylate, ethoxylated bisphenol-A (meth)acrylate, pentaerythritol (meth)acrylate, pentaerythritol (meth)acrylate, ditrimethylolpropane (meth)acrylate, ethoxylated trimethylolpropane (meth)acrylate, dipentaerythritol (meth)acrylate, alkoxylated glyceryl(meth)acrylate. Still further examples of hydrophilic monomers are the vinyl carbonate and vinyl carbamate monomers disclosed in U.S. Pat. No. 5,070,215, and the hydrophilic oxazolone monomers disclosed in U.S. Pat. No. 4,910,277. The contents of these patents are incorporated herein by reference. The hydrophilic monomer also can be an anionic monomer, such as 2-methacryloyloxyethylsulfonate salts. Substituted anionic hydrophilic monomers, such as from acrylic and methacrylic acid, can also be utilized wherein the substituted group can be removed by a facile chemical process. Non-limiting examples of such substituted anionic hydrophilic monomers include trimethylsilyl esters of (meth)acrylic acid, which are hydrolyzed to regenerate an anionic carboxyl group. The hydrophilic monomer also can be a cationic monomer selected from the group consisting of 3-methacrylamidopropyl-N,N,N-trimethyammonium salts, 2-methacryloyloxyethyl-N,N,N-trimethylammonium salts, and amine-containing monomers, such as 3-methacrylamidopropyl-N,N-dimethyl amine. Other suitable hydrophilic monomers will be apparent to one skilled in the art.

Non-limiting examples of hydrophobic monomers are $C_1$-$C_{20}$ alkyl and $C_3$-$C_{20}$ cycloalkyl(meth)acrylates, substituted and unsubstituted aryl (meth)acrylates (wherein the aryl group comprises 6 to 36 carbon atoms in the ring system), (meth)acrylonitrile, styrene, lower alkyl styrene, lower alkyl vinyl ethers, fluoro-containing olefins, and $C_2$-$C_{10}$ perfluoroalkyl(meth)acrylates and correspondingly partially fluorinated (meth)acrylates.

Other non-limiting examples of additional monomers are fluorinated amphiphilic monomers, such as fluorosulfonate-containing olefins represented by the formula $CX_2=CX$-$L$-$SO_3J$, or fluorocarbonate-containing olefins represented by the formula $CX_2=CX$-$L$-$C(O)OJ$, wherein X is hydrogen, fluorine, or $R^3$ (defined previously); L is perfluoroalkylene, alkylene, ether, arylene, perfluoroarylene, branched alkylene, or combinations thereof; and J is hydrogen or an alkali metal. Non-limiting examples of the fluorinated monomers are Nafion® perfulorinated ionomer having the formula of

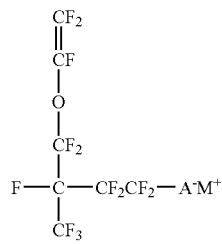

wherein A is either sulfonic or carboxylic functional group and M is either a metal cation in the neutralized form or $H^+$ in the acid form; (trifluorovinyloxy)benzoic acid; (trifluorovinyloxy)sulfonic acid; and alkali salts thereof.

Solvents useful in the preparation of a monomer mixture include toluene, xylene, alcohols, lactams, amides, cyclic ethers, linear ethers, carboxylic acids, and combinations thereof. Suitable solvents include tetrahydrofuran ("THF"), acetonitrile, N,N-dimethyl formamide ("DMF"), toluene, and xylene.

In one embodiment, a polymeric material suitable for the preparation of an ophthalmic lens having high oxygen permeability (such as Dk of about 60, 70, 80 barrers, or higher) can comprise: (a) units of a divinyl-functionalized fluorinated ketal monomer (having Formula VII) or units of a vinyl-functionalized fluorinated dioxole (having Formula XIII) or combinations thereof; and (b) units of monovinyl- or divinyl-terminated polysiloxane, such as monovinyl- or divinyl-terminated polydimethylsiloxane or monovinyl- or divinyl-terminated polymethylphenylsiloxane. Such a vinyl-terminated polysiloxane also can have fluorinated side groups to reduce lipid and/or protein deposits. In another embodiment, such a vinyl-terminated polysiloxane has a side group that comprises an aromatic group having 6-36 carbon atoms in the ring system, for example to increase the refractive index of the polymeric material.

In another embodiment, a hydrophilic vinylic monomer also can be included in a formulation for the preparation of the ophthalmic lens. Non-limiting examples of such a hydrophilic vinylic monomer are vinyl carbonate, vinyl carbamate, and oxazolone disclosed above.

The present invention also provides a method for producing a medical device. In one aspect, the method comprises: (a) providing a composition comprising a vinyl functionalized fluorinated ketal monomer or a vinyl functionalized fluorinated dioxole monomer; and (b) forming the medical device from the composition.

In one embodiment, the step of forming comprises: (i) disposing the composition in a mold, which has a cavity having the shape of the medical device; and (ii) polymerizing the composition to form the medical device.

In another embodiment, the step of forming comprises: (i) polymerizing the composition to form a solid block; and (ii) shaping the block to form the medical device.

In still another embodiment, the step of shaping comprises cutting the block into wafers; and lathing or machining the wafer into the shape of the medical device.

In yet another embodiment, the step of polymerizing the composition is carried out in the presence of a thermal polymerization initiator or a photo polymerization initiator. The thermal polymerization may be carried out at temperature in the range from slightly higher than room temperature (such as about 30° C.) to about 120° C., or from about 30° C. to about 100° C. The time for complete polymerization may range from about 5 minutes to about 24 hours, or from about 5 minutes to about 10 hours, or from about 10 minutes to about 5 hours.

In some embodiments, the medical devices produced in a method, or from a polymeric material, of the present invention can be contact lenses, intraocular lenses, corneal inlays, corneal rings, or keratoprotheses.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A medical device comprising a polymeric composition that comprises units of fluorinated dioxole that has a formula selected from the group consisting of

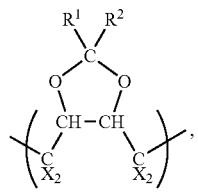 (I)

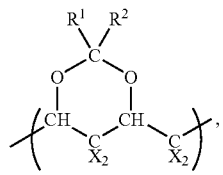 (II)

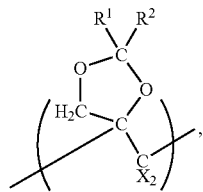 (III)

and combinations thereof, wherein X is independently selected from the group consisting of hydrogen, fluorine, and $R^1$, $R^2$ are independently selected from the group consisting of substituted and unsubstituted lower alkyl groups, substituted and unsubstituted alkyloxy groups, substituted and unsubstituted aromatic and heteroaromatic groups having 6-36 carbon atoms in a ring system, substituted and unsubstituted cyclic and heterocyclic groups having 6-36 carbon atoms in a ring system, and combinations thereof; and at least one of the groups $R^1$, $R^2$, and X comprises a fluorinated group and at least one of $R^1$, $R^2$ comprises a substituted or unsubstituted aromatic group having 6-36 carbon atoms in a ring system.

2. The medical device of claim 1, wherein X is fluorine.

3. The medical device of claim 1, wherein the polymeric composition comprises units of fluorinated dioxole having Formula I, II, or combinations thereof.

4. The medical device of claim 1, wherein the polymeric composition comprises units of fluorinated dioxole having Formula III.

5. The medical device of claim 1, wherein the polymeric composition comprises units of an additional monomer selected from the group consisting of hydrophobic monomers, hydrophilic monomers, combinations thereof, and mixtures thereof.

6. The medical device of claim 1, wherein the polymeric composition comprises units of a vinyl-terminated polysiloxane, wherein the polysiloxane comprises a side group that comprises an aromatic group having 6-36 carbon atoms in a ring system.

7. The medical device of claim 6, wherein the polysiloxane comprises a side group that comprises a fluorinated lower alkyl group.

8. The medical device of claim 6, wherein the polymeric composition comprises units of a hydrophilic monomer.

9. The medical device of claim 1, wherein the medical device is a contact lens, an intraocular lens, a corneal inlay, a corneal ring, or a keratoprothesis.

* * * * *